(12) United States Patent
Allmendinger et al.

(10) Patent No.: US 7,872,153 B2
(45) Date of Patent: Jan. 18, 2011

(54) SALT OF ALISKIREN WITH SULFURIC ACID

(75) Inventors: Thomas Allmendinger, Lörrach (DE); Frank Stowwasser, Murg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/293,162

(22) PCT Filed: Mar. 19, 2007

(86) PCT No.: PCT/EP2007/002415

§ 371 (c)(1),
(2), (4) Date: Sep. 16, 2008

(87) PCT Pub. No.: WO2007/107317

PCT Pub. Date: Sep. 27, 2007

(65) Prior Publication Data

US 2009/0088479 A1  Apr. 2, 2009

(30) Foreign Application Priority Data

Mar. 21, 2006  (GB) .................................. 0605688.1

(51) Int. Cl.
*C07C 233/05* (2006.01)
*A61K 31/165* (2006.01)

(52) U.S. Cl. ...................................... 564/157; 514/616

(58) Field of Classification Search ................. 564/157; 514/616

See application file for complete search history.

(56) References Cited

U.S. PATENT DOCUMENTS

| | | | |
|---|---|---|---|
| 5,559,111 A | 9/1996 | Göschke et al. | 514/227.5 |
| 5,606,078 A | 2/1997 | Göschke et al. | 549/321 |
| 5,627,182 A | 5/1997 | Göschke et al. | |
| 5,646,143 A | 7/1997 | Göschke et al. | 514/233.8 |
| 5,654,445 A | 8/1997 | Göschke et al. | 549/321 |
| 5,659,065 A | 8/1997 | Göschke et al. | 560/29 |
| 5,705,658 A | 1/1998 | Göschke et al. | 549/321 |

FOREIGN PATENT DOCUMENTS

| | | |
|---|---|---|
| EP | 0 678 503 | 10/1995 |
| WO | WO 02/02508 | 1/2002 |
| WO | WO 2005/089729 | 9/2005 |

OTHER PUBLICATIONS

West, Anthony R., Solid State Chemistry and its Applications, Wiley, New York, 1988, pp. 358 & 365.*
Stahl et al., eds., Handbook of pharmaceutical salts. Properties, selection and use (Wiley-VCH, 2008), pp. 265-327.*

* cited by examiner

*Primary Examiner*—Shailendra Kumar
(74) *Attorney, Agent, or Firm*—Ann R. Pokalsky, Esq.; Dilworth & Barrese, LLP

(57) ABSTRACT

The invention relates to a new salt of aliskiren, the respective production and usage, and pharmaceutical preparations containing such a salt.

5 Claims, No Drawings

SALT OF ALISKIREN WITH SULFURIC ACID

This application is a 371 of PCT/EP2007/002415, filed Mar. 19, 2007.

The invention relates to a new salt of the renin inhibitor 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide of formula

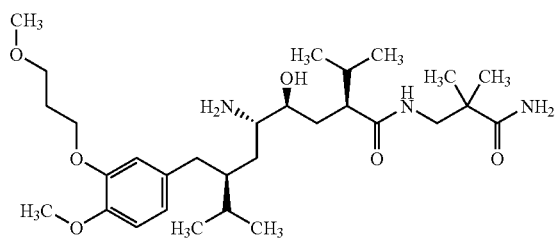

This compound has the INN name aliskiren is specifically disclosed in EP 678503 A.

The active ingredient aliskiren is the free base which is described specifically in EP 678503 A and it has one basic group, the amino group in position 5. This group has a pKa of 9.79. Accordingly, one acidic group can bind to the nitrogen lone pairs of the amino group.

EP 678503 A, discloses the hydrochloride salt (example 137) and the hemifumarate salt (example 83) as specific salts of aliskiren. However, it does not mention any special properties of these salts. Meanwhile, the active ingredient aliskiren in the form of the hemifumarate salt is in development as an anti-hypertensive agent. In contrast to the free base and the HCl salt, the hemifumarate salt is easier to handle, has the ability to crystallize at least partially and this salt was readily available. Moreover, it was postulated in the art that strong acids in contrast to weak acids do not produce a stable salt with aliskiren.

The hemifumarate salt has a melting point in an open crucible of 96.6° C. (10 K/min heating rate) and a melting enthalpy of 28.9 J·g$^{-1}$.

Aliskiren hemifumarate is difficult to formulate. Typically, in a galenic formulation comprising aliskiren hemifumarate, a high amount is normally needed of the drug substance (DS) with properties that make the formulation of tablets difficult.

For example, aliskiren hemifumarate has a needle shaped crystal habit, which has a negative influence on the bulk properties of the drug substance, e.g., flow properties and bulk density. The compression behavior of the drug substance is poor, leading to weak interparticulate bonds and polymorphism changes under pressure and/or amorphization under compression. Aliskiren hemifumarate has a strong elastic component that also leads to weakening of interparticulate bonds. The high dose (up to 300 or 600 mg of the free base per tablet) makes a high drug loading necessary in order to achieve a reasonable tablet size.

The drug substance quality is very variable with effect on the processability of a tablet, e.g., particle size distribution, bulk density, flowability, wetting behavior, surface area and sticking tendency. Moreover, aliskiren is highly hygroscopic. In contact with water, the drug substance polymorphism changes to an amorphous state, which shows inferior stability compared to the crystalline state. The combination of these hurdles makes a standard tablet manufacturing process extremely difficult.

Direct compression is not a feasible option for routine production because of, e.g., the high hygroscopicity, the needle shaped particle structure, the poor flowability with resulting processability problems and dose uniformity problems. A roller compaction process leads to a reduction of the high bulk volume of the drug substance. Yet, the pre-compression of the drug substance during roller compaction makes a further compression into tablets with sufficient hardness and resistance to friability without a high amount of excipients extremely difficult due to the low compressibility of the drug substance. A tablet with a drug load of aliskiren higher than ca. 35% has been found not to lead to robust tablets (e.g. friability, hardness) and a robust process (e.g. sticking and picking during roller compaction and tabletting).

As explained above, the low crystallinity, hygroscopicity and relatively low stability, in particular in the presence of moisture, leads to a more complicated manufacturing process in particular when isolating the final product. Specifically processes such as filtration and drying can be very long as a result of the above-mentioned less desirable properties of aliskiren hemifumarate. Aliskiren hemifumarate is also sensitive to the granulation process.

Therefore, despite the very major contribution which aliskiren has made, the reported undesirable properties have been an impediment with respect to the process economy.

Therefore, there is a need for more stable, e.g. crystalline forms of aliskiren, which are even easier to manage in the drying, filtration or granulation processes following the final stage of the chemical preparation process and also in the steps for preparing the pharmaceutical formulations. Many futile attempts have been made to find improved forms through salt formation, the forms ideally being as crystalline as possible, as well as physically and chemically stable. Only the salt according to the invention, its solvates and polymorphous forms thereof exhibit the desired improved properties.

The formation of salts of aliskiren with the desired advantageous properties has proved to be difficult. In the majority of cases, for example, amorphous salts with little stability are obtained (such as hard foams, waxes or oils). Extensive research has shown that the salt of aliskiren according to the invention have proved to be particularly advantageous compared with the hemifumarate salt of aliskiren.

The present invention relates to a salt of a compound of formula I

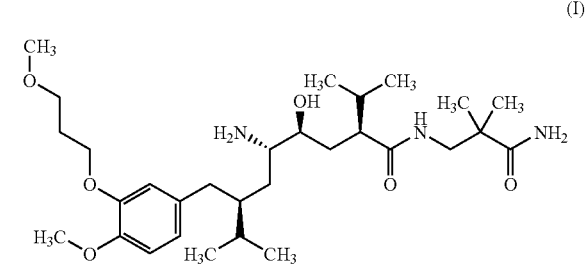

with sulfuric acid, or respectively, an amorphous form, a solvate, especially hydrate, as well as a polymorphous form thereof.

Preferred salts are for example selected from the sulfate salt ($SO_4^{2-}$) and the hydrogen sulfate salt ($HSO_4^-$). In the case of the sulfate salt, there are two molecules of aliskiren per one mole of sulfate present. In the case of the hydrogen sulfate salt, there is one molecule of aliskiren per one mole of hydrogen sulfate present. More preferably, the salt is the hydrogen sulfate salt.

Preferred salts are for example selected from the salt of aliskiren in amorphous form; or salt of aliskiren in crystalline or partly crystalline form, especially in solvate form, thereof.

The salt according to the invention preferably exist in isolated and essentially pure form, for example in a degree of purity of >95%, preferably >98%, primarily >99%. The enantiomer purity of the salts according to the invention is >98%, preferably >99%.

Compared with the hemifumarate, the salt according to the invention, including the amorphous forms, solvates such as salt hydrates, and also the corresponding polymorphous forms thereof, has unexpectedly advantageous properties. Under given conditions, the salt, in particular the crystalline or partially crystalline salt including salt solvates, has a clear melting point which is linked with a marked, endothermic melting enthalpy. The salt according to the invention, in particular the crystalline or partially crystalline form thereof, is stable and is of better quality than aliskiren hemifumarate also during storage and distribution.

In addition, both the crystalline and the amorphous salts according to the invention are less hygroscopic than the hemifumarate salt, in particular below 40% relative humidity. Thus, the salt according to the invention has proved to be physically stable. This is considered to be mainly due to the fact that although the melting points of both salts are comparable, the melting enthalpy of the salt according to the invention is considerably higher.

Improved physicochemical properties of certain salts or certain salt solvates are of great importance both when they are produced as a pharmaceutically active substance and when producing, storing and applying the galenic preparation. In this way, starting with improved constancy of the physical parameters, an even higher quality of the formulations can be guaranteed. The high stability of the salt or salt solvates also give the possibility of attaining economic advantages by enabling simpler process steps to be carried out during working up. The preferable high crystallinity of the salt or salt solvate allows the use of a choice of analytical methods, especially the various X-ray methods, the usage of which permits a clear and simple analysis of their release to be made. This factor is also of great importance to the quality of the active substance and its galenic forms during production, storage and administration to the patients. In addition, complex provisions for stabilising the active ingredient in the galenic formulations can be avoided.

Thus, it was unexpectedly found that contrary to general knowledge, a strong acid, namely sulfuric acid can form a stable salt with aliskiren.

The invention accordingly relates to crystalline, also partly crystalline and amorphous salts of aliskiren. Preferably, The salt has a degree of crystallinity of more than 30%, more preferably more than 40%, yet more preferably more than 50% such as 55-60%.

As well as the solvates, such as hydrates, the invention also relates to polymorphous forms of the salts according to the invention.

Solvates and also hydrates of the salts according to the invention may be present, for example, as hemi-, mono-, di-, tri-, tetra-, penta-, hexa-solvates or hydrates, respectively. Solvents used for crystallisation, such acetonitrile, alcohols, especially methanol, ethanol, aldehydes, ketones, especially acetone, esters, e.g. ethyl acetate, or alkanes, especially pentane, hexane, heptane or cyclohexane, may be embedded in the crystal grating. A preferred solvate is a solvate of acetonitrile. The extent to which a selected solvent or water leads to a solvate or hydrate in crystallisation and in the subsequent process steps or leads directly to the free base is generally unpredictable and depends on the combinations of process conditions and the various interactions between aliskiren and the selected solvent, especially acetonitrile. The respective stability of the resulting crystalline or amorphous solids in the form of salts, solvates and hydrates, as well as the corresponding salt solvates or salt hydrates, must be determined by experimentation. It is thus not possible to focus solely on the chemical composition and the stoichiometric ratio of the molecules in the resulting solid, since under these circumstances both differing crystalline solids and differing amorphous substances may be produced.

The salt solvates or hydrates may be preferred, as solvent or water molecules in the crystal structure are bound by strong intermolecular forces and thereby represent an essential element of structure formation of these crystals which, in part, are extraordinarily stable. This is in stark contrast to the hemifumarate salt where any solvate formed is instable. However, solvent or water molecules are also existing in certain crystal lattices which are bound by rather weak intermolecular forces. Such molecules are more or less integrated in the crystal structure forming, but to a lower energetic effect. The solvent or water content in amorphous solids can, in general, be clearly determined, as in crystalline solvates or hydrates, but is heavily dependent on the drying and ambient conditions. In contrast, in the case of stable solvates or hydrates, there are clear stoichiometric ratios between the pharmaceutical active substance and the solvent or water. In many cases these ratios do not fulfil completely the stoichiometric value, normally it is approached by lower values compared to theory because of certain crystal defects. The ratio of organic molecules to solvent or water molecules for the weaker bound water may vary to a considerable extend, for example, extending over di-, tri- or tetra-hydrates. On the other hand, in amorphous solids, the molecular structure classification of solvent or water is not stoichiometric; the classification may however also be stoichiometric only by chance.

In some cases, it is not possible to classify the exact stoichiometry of the solvent or water molecules, since layer structures form so that the embedded solvent or water molecules cannot be determined in defined form.

In one preferred embodiment there are two parts of solvate to three parts of the salt.

For the crystalline solids having identical chemical composition, the different resulting crystal gratings are summarized by the term polymorphism.

Any reference hereinbefore and hereinafter, to the salts according to the invention is to be understood as referring also to the corresponding solvates, such as hydrates, and polymorphous modifications, and also amorphous forms, as appropriate and expedient.

The X-ray diffraction diagram of powders of the salt has a number of discrete X-ray reflections, and signs of non-crystalline or amorphous portions. The degree of crystallinity is surprisingly high.

This process for determining the structure of a crystal enables, under normal conditions such as high physical, chemical and enantiomeric purity of the gauged crystals, a clear determination of the structure to be carried out on a molecular or atomic level, namely symmetry and size of the elementary cells, atom positions and temperature factors, and from the ascertained cell volume, the X-ray density is shown on the basis of a molecular weight. At the same time, the X-ray structure determination supplies details of its quality.

In an open specimen container, for a heating rate of $T_r=10$ K·min$^{-1}$ it has a melting point of 97.1° C. and a melting enthalpy of 39.3 J·$^{-1}$. The indicated melting point is a melting point which can only be measured in an open specimen container.

These two thermodynamic characteristics illustrate the advantageous physical properties, compared to the hemifumarate, with the two corresponding data, namely a melting point in the open system of 96.6° C. and a melting enthalpy of 28.9 J·$^{-1}$. These thermodynamic data prove the high stability of this crystal grating. They are the foundation for the special physical and chemical resistance of the hydrogen sulfate salt of aliskiren.

A measurement of the infrared absorption spectrum of the hydrogen sulfate salt of aliskiren in a potassium bromide compressed tablet shows the following significant bands expressed in reciprocal wave numbers (cm.sup.-1): The intensities of the absorption bands are indicated as follows: (w)=weak; (m)=medium; and (st)=strong intensity. Measurement of the infrared spectrum likewise took place by means an FTIR-microscope in transmission using the microscope Hyperion by Bruker Optics, Germany.

The error margin for all absorption bands of ATR-IR is ±2 cm$^{-1}$. 3353 (br), 3078, 2960, 2935, 2876, 1660 (C=O), 1516 (amid II), 1470, 1444, 1425, 1389, 1371, 1260, 1234 (Aryl-O), 1191, 1163, 1140, 1047, 872, 809, 768, 723

Further characterisation of the hydrogen sulfate salt of aliskiren is effected using the interlattice plane intervals determined by a X-ray powder pattern. Measurement of the X-ray powder patterns was made with a Scintag XDS2000 powder diffractometer in reflection geometry, using Cu—Ka$_{1+2}$ radiation with a energy dispersive detector at room temperature. The preferred characterisation of the hydrogen sulfate salt of aliskiren is obtained from the interlattice plane intervals d of the ascertained X-ray diffraction diagrams, whereby, in the following, average values are indicated with the appropriate error limits.

The most intensive reflections in the X-ray diffraction diagram show the following interlattice plane intervals:

d in [Å] (±0.1 Å): 21.3, 12.4, 10.7, 10.1, 8.4, 7.9, 6.7, 6.0, 5.3, 4.9, 4.7, 4.5, 4.4, 4.1.

An essential feature for the quality of a pure active substance both for the physical-chemical procedures such as drying, sieving, grinding, and in the galenic processes which are carried out with pharmaceutical excipients, namely in mixing processes, in granulation, in spray-drying, in tabletting, is the water absorption or water loss of this active substance depending on temperature and the relative humidity of the environment in question. With certain formulations, free and bound water is without doubt introduced with excipients and/or water is added to the process mass for reasons associated with the respective formulation process. In this way, the pharmaceutical active substance is exposed to free water over rather long periods of time, depending on the temperature of the different activity (partial vapour pressure).

A clear characterisation of this property is achieved by means of isothermal measurements over predetermined time intervals and predetermined relative humidity using dynamic vapour sorption (DVS from the company Surface Measurement Systems LTD, Marlow, Buckinghamshire, UK). Table 4 illustrates the mass change, i.e. the water absorption or loss as a function of relative humidity at 25° C. for a sample of 9.5 mg of the hydrogen sulfate salt of aliskiren and for a period of 4 hours. The following cycles of changes in relative humidity are shown: 40-0; 0-95% relative humidity:

TABLE 4

| relative humidity in % | change in mass in % (desorption) | relative humidity in % | change in mass in % (sorption) |
|---|---|---|---|
| 40 | 2.20 | 0 | 0.00 |
| 30 | 1.67 | 10 | 0.46 |
| 20 | 1.25 | 20 | 0.84 |
| 10 | 0.88 | 30 | 1.31 |
| 0 | 0.00 | 40 | 1.98 |
|  |  | 50 | 3.39 |
|  |  | 60 | 7.07 |
|  |  | 70 | 8.88 |
|  |  | 80 | 13.43 |
|  |  | 90 | 25.83 |
|  |  | 95 | 40.62 |

The measurement error of this sorption method based on thermogravimetry is about 0.1%. Therefore, the hydrogen sulfate salt of aliskiren under the conditions employed, which are realistic from a pharmaceutical-galenic point of view, shows significant water absorption or loss above 40% relative humidity. This is comparable to a large extent to the given properties of the hemifumarate, but below 40% relative humidity the hydrogen sulfate salt of aliskiren does not take up as much water as the hemifumarate. This property is important in the final stages of chemical manufacture and also in practice in all galenic process stages of the different dosage forms.

Owing to the advantageous properties of the hydrogen sulfate salt, this salt is suitable for pressing directly to form corresponding tablet formulations.

In addition to the good physicochemical properties of the hydrogen sulfate salt, it is also of advantage to use this salt in order to improve and simplify the overall manufacture process of the drug. For example when employing e.g. the process as disclosed in EP 678503 A, the hemifumarate salt must be formed in a separate step after N-deprotection. When employing sulfuric acid, however, the N-deprotection and the salt formation can be performed in a single step, thus, rendering the manufacturing process more efficient.

A further object of the invention is the preparation of the salts according to the invention.

The salts according to the invention, including amorphous or crystalline forms thereof, may be prepared as follows:

To form the salt, the process is carried out in a solvent system, in which the two reactants, namely the base aliskiren and the respective acid, are sufficiently soluble. It is expedient to use a solvent or solvent mixture, in which the resulting salt is only slightly soluble or not soluble at all, in order to achieve crystallisation or precipitation. One variant for the salt according to the invention would be to use a solvent in which this salt is very soluble, and to subsequently add an antisolvent to this solution, that is a solvent in which the resulting salt has only poor solubility. A further variant for salt crystallisation consists in concentrating the salt solution, for example by heating, if necessary under reduced pressure, or by slowly evaporating the solvent, e.g. at room temperature, or by seeding with the addition of seeding crystals, or by setting up water activity required for hydrate formation.

The solvents that may be used are for example $C_3$-$C_7$alkylnitriles, especially acetonitrile, $C_1$-$C_5$-alkanols, preferably ethanol and isopropanol, esters, especially $C_2$-$C_7$-alkanecarboxylic acid-$C_1$-$C_5$-alkylester, such as ethyl or isopropyl acetate, di-($C_1$-$C_5$-alkyl)-ethers, such as tert.-butylmethylether, furthermore tetrahydrofuran, and $C_5$-$C_8$-alkanes, especially pentane, hexane, cyclohexane or heptane and mixtures of these solvents with water. The most referred solvent is acetonitrile.

To produce hydrates, a dissolving and crystallizing process is used in particular, or a water-equilibrating crystallisation process.

The dissolving and crystallizing process is characterised in that (i) aliskiren free base is dissolved in an organic solvent, (ii) sulfuric acid, preferably as an aqueous solution, is added to the solution obtained in (i), (iii) the solution left standing to induce crystallization, (iv) the crystals are filtered and dried, to obtain the salt.

In the dissolving process (i), the organic solvent employed is advantageously an alcohol, such as ethanol or isopropanol, or an alkylnitrile, especially acetonitrile, and water. If necessary, the solvent may be warmed to above room temperature to, e.g. 25 to 60° C., more preferably 30 to 50° C.

In the process step (ii), the aqueous solution employed is advantageously a 10 to 30%, more preferably a 15 to 25%, such as a 20%, solution of sulfuric acid.

In the process step (iii), the solution is advantageously left standing so as to slowly evaporate off the solvent. This is preferably conducted by cooling to room temperature or below, more preferably to −10 to 20° C., still more preferably −5 to 10° C., most preferably 0 to 5° C. The concentration of the solution can also take place by warming to above room temperature, e.g. to >25 to 100° C., more preferably 30 to 70° C. It is typically left standing for 8 to 48 h, preferably 17 to 36 h, most preferably 20 to 30 h.

In the process step (iv), the drying is preferably effected at elevated temperatures, more preferably 20 to 50° C., most preferably 30 to 40° C. The pressure is preferably selected to be 1 to 100 mbar, preferably 10 to 50 mbar, more preferably 20 to 40 mbar, such as 30 mbar. The drying typically takes place until a constant mass is obtained. Depending on the drying conditions, the drying may take from 5 to 48 h, preferably 10 to 24 h such as 15 to 20 h.

The processes for forming salts are likewise objects of the present invention.

In a preferred variant, crystallisation may be optimised, e.g. accelerated, by adding at least one seed crystal.

The salts according to the invention may be used e.g. in the form of pharmaceutical preparations, which contain the active substance e.g. in a therapeutically effective amount of the active substance, optionally together with a pharmaceutically acceptable carrier, for example with an inorganic or organic, solid or optionally also liquid pharmaceutically acceptable carrier, which is suitable for enteral, e.g. oral, or parenteral administration.

The invention relates in particular to a pharmaceutical composition, especially in a solid dosage unit, preferably for oral administration, optionally together with a pharmaceutically acceptable carrier.

Pharmaceutical preparations of this kind may be used for example for the prophylaxis and treatment of diseases or conditions which may be inhibited by blocking the $AT_1$ receptor for example a disease or condition selected from the group consisting of (a) hypertension, congestive heart failure, renal failure, especially chronic renal failure, restenosis after percutaneous transluminal angioplasty, and restenosis after coronary artery bypass surgery;

(b) atherosclerosis, insulin resistance and syndrome X, diabetes mellitus type 2, obesity, nephropathy, renal failure, e.g. chronic renal failure, hypothyroidism, survival post myocardial infarction (MI), coronary heart diseases, hypertension in the elderly, familial dyslipidemic hypertension, increase of formation of collagen, fibrosis, and remodeling following hypertension (antiproliferative effect of the combination), all these diseases or conditions associated with or without hypertension;

(c) endothelial dysfunction with or without hypertension, (d) hyperlipidemia, hyperlipoproteinemia, atherosclerosis and hypercholesterolemia, and (e) glaucoma.

Primary usages are for the treatment of high blood pressure and congestive heart failure, as well as post-myocardial infarction.

The person skilled in the pertinent art is fully enabled to select a relevant and standard animal test model to prove the hereinbefore and hereinafter indicated therapeutic indications and beneficial effects.

The pharmaceutical activities as effected by administration of representatives of the salts of the present invention or of the combination of active agents used according to the present invention can be demonstrated e.g. by using corresponding pharmacological models known in the pertinent art. The person skilled in the pertinent art is fully enabled to select a relevant animal test model to prove the hereinbefore and hereinafter indicated therapeutic indications and beneficial effects.

Drug efficacy is assessed in various animal models including the deoxycorticosterone acetate-salt rat (DOCA-salt) and the spontaneously hypertensive rat (SHR), either maintained on a normal salt diet or with salt loading (4-8% salt in rat chow or 1% NaCl as drinking water).

The DOCA-salt test model utilizes either an acute or chronic study protocol. An acute study procedure involves assessment of the effects of various test substances over a six-hour experimental period using rats with indwelling femoral arterial and venous catheters. The Acute Study Procedure evaluates test substances for their ability to reduce blood pressure during the established phase of DOCA-salt hypertension. In contrast, the Chronic Study Procedure assesses the ability of test substances to prevent or delay the rise in blood pressure during the development phase of DOCA-salt hypertension. Therefore, blood pressure will be monitored in the chronic study procedure by means of a radiotransmitter. The radiotransmitter is surgically implanted into the abdominal aorta of rats, prior to the initiation of DOCA-salt treatment and thus, prior to the induction of hypertension. Blood pressure is chronically monitored for periods of up 6 weeks (approximately one week prior to DOCA-salt administration and for 5 weeks thereafter).

Rats are anesthetized with 2-3% isoflurane in oxygen inhalant followed by Amytal sodium (amobarbital) 100 mg/kg, ip. The level of anesthesia is assessed by a steady rhythmic breathing pattern.

Acute Study Procedure:

Rats undergo a unilateral nephrectomy at the time of DOCA implantation. Hair is clipped on the left flank and the back of the neck and scrubbed with sterile alcohol swabs and povidone/iodine. During surgery rats are placed on a heating pad to maintain body temperature at 37° C.

A 20 mm incision is made through the skin and underlying muscle to expose the left kidney. The kidney is freed of surrounding tissue, exteriorized and two ligatures (3-0 silk)

are tied securely around the renal artery and vein proximal to their juncture with the aorta. The renal artery and vein are then severed and the kidney removed. The muscle and skin wounds are closed with 4-0 silk suture and stainless steel wound clips, respectively. At the same time, a 15 mm incision is made on the back of the neck and a 3-week-release pellet (Innovative Research of America, Sarasota, Fla.) containing deoxycorticosterone acetate (100 mg/kg) is implanted subcutaneously. The wound is then closed with stainless-steel clips and both wounds are treated with povidone/iodine; the rats are given a post-surgical intramuscular injection of procaine penicillin G (100,000 U) and buprenorphine (0.05-0.1 mg/kg) s.c. The rats are immediately placed on 1% NaCl+0.2% KCl drinking water; this treatment continues for at least 3 weeks at which time the animals have become hypertensive and available for experimentation.

Forty-eight hours prior to experimentation, animals are anesthetized with isoflurane and catheters are implanted in the femoral artery and vein for measuring arterial pressure, collection of blood, and administration of test compounds. Rats are allowed to recover for 48 hours while tethered in a Plexiglas home cage, which also serves as the experimental chamber.

Chronic Study Procedure:

This procedure is the same as above except that rats are implanted with a radiotransmitter, 7-10 days prior to the unilateral nephrectomy and initiation of DOCA and salt. In addition, rats do not undergo surgery for placement of femoral arterial and venous catheters.

Radiotransmitters are implanted as described by M. K. Bazil, C. Krulan and R. L. Webb. in J. Cardiovasc. Pharmacol. 22: 897-905, 1993.

Protocols are then set-up on the computer for measurement of blood pressure, heart rate, etc, at predetermined time points. Baseline data is collected at various time points and over various time intervals. For example, baseline or pre-dose values usually consist of data collection and averaging over 3 consecutive, 24-hour time periods prior to drug administration.

Blood pressure, heart rate and activity are determined at various pre-selected time points before, during, and after drug administration. All measurements are performed in unrestrained and undisturbed animals. The maximum study time, determined by battery life, could be as long as nine months. For studies of this duration, rats are dosed orally (1-3 ml/kg vehicle), no more than twice daily or drug is administered via the drinking water or mixed with food. For studies of a shorter duration, that is, up to 8 weeks, drugs are given via subcutaneously implanted osmotic minipumps. Osmotic minipumps are selected based on drug delivery rate and time. Aliskiren dosages (free base) range from 1 to 10 mg/kg/day.

Additionally, SHR are utilized to study the effects of aliskiren. The hypertensive background of the SHR is modified either by chronic salt loading in an effort to suppress the renin angiotensin system (RAS) or chronic salt depletion to activate the RAS in the SHR. These manipulations will be carried out to more extensively evaluate the efficacy of the various test substances. Experiments performed in spontaneously hypertensive rats (SHR) are supplied by Taconic Farms, Germantown, N.Y. (Tac:N(SHR)fBR). A radiotelemetric device (Data Sciences International, Inc., St. Paul, Minn.) is implanted into the lower abdominal aorta of all test animals between the ages of 14 to 16 weeks of age. All SHR are allowed to recover from the surgical implantation procedure for at least 2 weeks prior to the initiation of the experiments. Cardiovascular parameters are continuously monitored via the radiotransmitter and transmitted to a receiver where the digitized signal is then collected and stored using a computerized data acquisition system. Blood pressure (mean arterial, systolic and diastolic pressure) and heart rate are monitored in conscious, freely moving and undisturbed SHR in their home cages. The arterial blood pressure and heart rate are measured every 10 min for 10 seconds and recorded. Data reported for each rat represent the mean values averaged over a 24 hour period and are made up of the 144-10 min samples collected each day. The baseline values for blood pressure and heart rate consist of the average of three consecutive 24 hour readings taken prior to initiating the drug treatments. All rats are individually housed in a temperature and humidity controlled room and are maintained on a 12 hour light dark cycle.

In addition to the cardiovascular parameters, weekly determinations of body weight also are recorded in all rats. Treatments are administered in the drinking water, via daily oral gavage or in osmotic minipumps as stated above. If given in drinking water, water consumption is measured five times per week. Aliskiren doses (free base) for individual rats are then calculated based on water consumption for each rat, the concentration of drug substance in the drinking water, and individual body weights. All drug solutions in the drinking water are made up fresh every three to four days. Typical dosages for aliskiren (free base) in drinking water range from 3 to 30 mg/kg/day. However, in cases wherein the responder rate is increased with combination treatment, the dosages are identical to those used as monotherapy.

When drugs are administered by oral gavage, the dose of aliskiren (free base) ranges from 1 to 50 mg/kg/day.

Upon completion of the chronic studies, SHR or DOCA-salt rats are anesthetized and the heart rapidly removed. After separation and removal of the atrial appendages, left ventricle and left plus right ventricle (total) are weighed and recorded. Left ventricular and total ventricular mass are then normalized to body weight and reported. All values reported for blood pressure and cardiac mass represent the group mean±sem.

Vascular function and structure are evaluated after treatment to assess the beneficial effects of the combination. SHR are studied according to the methods described by Intengan H D, Thibault G, Li J S, Schiffrin E L, Circulation 100 (22): 2267-2275, 1999. Similarly, the methodology for assessing vascular function in DOCA-salt rats is described in Intengan H D, Park J B, Schiffrin, E L, Hypertension 34 (4 Part 2): 907-913, 1999.

The present pharmaceutical preparations which, if so desired, may contain further pharmacologically active substances, are prepared in a manner known per se, for example by means of conventional mixing, granulating, coating, dissolving or lyophilising processes, and contain from about 0.1% to 100%, especially from about 1% to about 50%, of lyophilisates up to 100% of the active substance.

The invention similarly relates to compositions containing the salts according to the invention.

The invention similarly relates to the use of the salts according to the invention preferably for the production of pharmaceutical preparations, especially for the prophylaxis and also for the treatment of diseases or conditions which may be modulated by renin inhibition. Primary usages are for the treatment of high blood pressure, renal failure, Left ventricular dysfunction and heart failure.

The invention similarly relates to the use for the prophylaxis and treatment of diseases or conditions which may be modulated by renin inhibition, characterised in that a patient, including a human patient, requiring such treatment is administered with a therapeutically effective amount of a salt according to the invention, optionally in combination with at least one composition for the treatment of cardiovascular diseases and related conditions and diseases listed hereinbefore or hereinafter.

The invention similarly relates to combinations, e.g. pharmaceutical combinations, containing a salt of the present invention or in each case a pharmaceutically acceptable salt thereof in combination with at least one composition for the treatment of cardiovascular diseases and related conditions and diseases as listed hereinbefore or hereinafter, or in each case a pharmaceutically acceptable salt thereof. Combinations with other compositions for the treatment of cardiovascular diseases and related conditions and diseases as listed hereinbefore or hereinafter, or in each case a pharmaceutically acceptable salt thereof, are likewise objects of the present invention.

The combination may be made for example with the following compositions, selected from the group consisting of a:

(i) HMG-Co-A reductase inhibitor or a pharmaceutically acceptable salt thereof, (ii) angiotensin converting enzyme (ACE) Inhibitor or a pharmaceutically acceptable salt thereof, (iii) calcium channel blocker or a pharmaceutically acceptable salt thereof, (iv) aldosterone synthase inhibitor or a pharmaceutically acceptable salt thereof, (v) aldosterone antagonist or a pharmaceutically acceptable salt thereof, (vi) dual angiotensin converting enzyme/neutral endopeptidase (ACE/NEP) inhibitor or a pharmaceutically acceptable salt thereof, (vii) endothelin antagonist or a pharmaceutically acceptable salt thereof, (viii) angiotensin II receptor blockers (ARB) or a pharmaceutically acceptable salt thereof, and (ix) diuretic or a pharmaceutically acceptable salt thereof.

HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs. Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating cortocosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

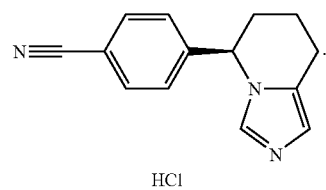

HCl

A preferred steroidal aldosterone antagonist is eplernone of the formula

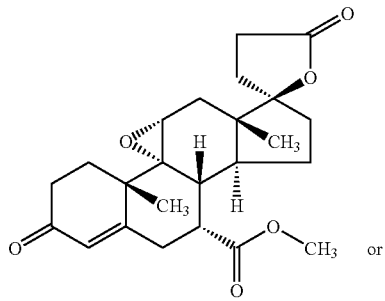

spironolactone.

A preferred dual angiotensin converting enzyme/neutral endopeptidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

Suitable angiotensin II receptor blockers which may be employed in the combination of the present invention include $AT_1$-receptor antagonists having differing structural features, preferred are those with the non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-4177 of the formula

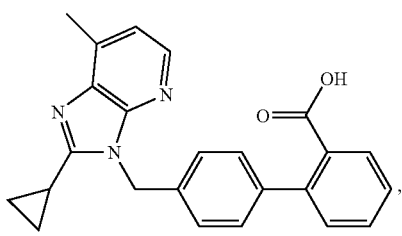

the compound with the designation SC-52458 of the following formula

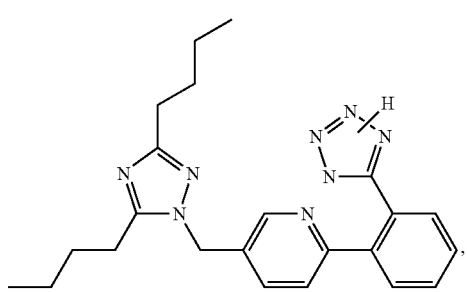

and the compound with the designation the compound ZD-8731 of the formula

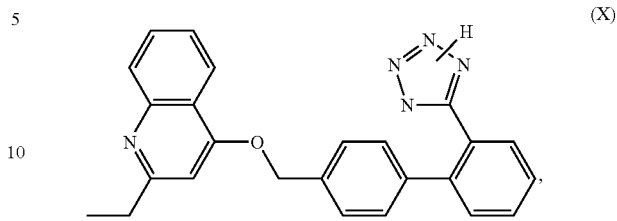

or, in each case, a pharmaceutically acceptable salt thereof.

Preferred $AT_1$-receptor antagonists are those agents that have reached the market, most preferred is valsartan, or a pharmaceutically acceptable salt thereof.

A diuretic is, for example, a thiazide derivative selected from the group consisting of chlorothiazide, hydrochlorothiazide, methylclothiazide, and chlorothalidon. The most preferred is hydrochlorothiazide.

Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The corresponding active ingredients or pharmaceutically acceptable salts thereof may also be used in form of a solvate, such as a hydrate or including other solvents, used for crystallization.

The compounds to be combined can be present as pharmaceutically acceptable salts. If these compounds have, for example, at least one basic center, they can form acid addition salts. Corresponding acid addition salts can also be formed having, if desired, an additionally present basic center. The compounds having an acid group (for example COOH) can also form salts with bases.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points. The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The invention furthermore relates to a commercial package comprising the combination according to the present invention together with instructions for simultaneous, separate or sequential use.

Dosaging of aliskiren (free base) may depend on various factors, such as mode of application, species, age and/or individual condition. For example, the doses to be administered to warm-blooded animals, including man, of approximately 75 kg body weight, especially the doses effective for the inhibition of renin activity, e.g., in lowering blood pressure, are from about 3 mg to about 3 g, preferably from about 10 mg to about 1 g, e.g., from 20 to 200 mg/person/day, divided preferably into 1 to 4 single doses which may, e.g., be of the same size. Usually, children receive about half of the adult dose. The dose necessary for each individual can be monitored, e.g., by measuring the serum concentration of the active ingredient, and adjusted to an optimum level. Single doses comprise, e.g., 75 mg, 150 mg or 300 mg per adult patient based on the free base.

The invention is illustrated in particular by the examples and also relates to the new compounds named in the examples and to their usage and to methods for the preparation thereof.

d in [Å]: 21.3, 12.4, 10.7, 10.1, 8.4, 7.9, 6.7, 6.0, 5.3, 4.9, 4.7, 4.5, 4.4, 4.1

A measurement of the 1H NMR spectrum in DMSO-$d_6$ a shows the following significant peaks:

$^1$H-NMR (400 MHz, DMSO-$d_6$): 0.81 (d, 6.8 Hz, 3H), 0.82 (d, 6.8 Hz, 3H), 0.86 (d, 6.6 Hz, 6H, H—C (l), H—C (m) and H—C (9)); 1.06 (s, 6H, h, h'); 1.25-1.8 (m, 6H, H—C (3, 6, 7, 8)); 1.95 (quintet, 2H, H—C (d)); 2.24 (m, 1H, H—C (2)); 2.45 (AB, 2H, H—C (b)); 2.69 (br.s, 1H, H—N (n')); 3.07 (dd, 5.5 Hz, 13.1 Hz, 2H) and 3.31 (dd, 6.8 Hz, 13.3 Hz, 2H, H—C (i)); 3.24 (s, 3H, H—C (f)); 3.71 (s, 3H, H—C (g)); 3.47 (t, 6.3 Hz, 2H, H—C (e)); 3.96 (t, 6.5 Hz, 2H, H—C (c)); 5.3 (br.s, 1H, OH); 6.68 (d, 8.1 Hz, 1H, H—C (a')); 6.67 (d, 1.8 Hz, 1H, H—C (a")); 6.82 (d, 8.1 Hz, 1H, H—C (a)); 6.83 and 7.13 (s, 1H each, H—N (n)); 7.46 (br. t, 1H, H—N (n'); 7.6 (very broad s, 3H, $H_3N^+$).

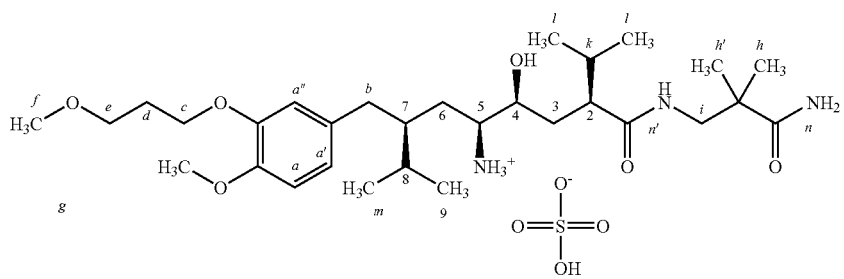

The following examples serve to illustrate the invention without limiting the invention in any way.

EXAMPLE 1

Production of the hydrogen sulfate salt of (2(S),4(S), 5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide 11 g (2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide free base (0.019 mol) was dissolved in acetonitrile (10 ml). To this solution was added dropwise with stirring an aqueous solution of sulfuric acid (4.9 g, 20% solution, 0.01 mol). The solution was cooled (0-5° C.) over a period of 1 h and kept for several hours, typically 10 to 48 h at this temperature to induce crystallization. The crystals are filtered and dried in vacuum (house vacuum 39 mbar, 40° C., 18 h) to obtain 8.21 g of the colorless salt.

The melting point for the sulfate salt of aliskiren, produced according to example 1, in an open crucible is 96.6° C. (10 K/min heating rate) with a melting enthalpy of 28.9 J·$g^{-1}$.

The enantiomer purity of the salt produced according to example 1 is determined by a stereo-specific HPLC method. The stereo-specific separation is achieved by a chiral column (Chiral AGP). The enantiomer purity is determined as ee=100%.

Calculation of the interlattice plane intervals from the X-ray powder pattern taken with a Scintag XDS2000 powder diffractometer is as follows for the most important lines for this batch of the sulfate salt of aliskiren:

Elementary analysis gives the following measured values of the elements present aliskiren hydrogen sulfate and of acetonitrile. The findings of the elementary analysis, within the error limits, correspond to the sum formula $3*(C_{30}H_{53}N_3O_6*HSO_3)+2*CH_3CN$—the hydrogen-sulfate salt containing acetonitrile (40 mol % or 4% g).

Found C, 55.00% H, 8.34% N, 7.57% O: 23.66% S: 4.60%
Calculated*C, 55.66% H, 8.34% N, 7.57% O: 23.66% S: 4.74%

What we claim is:
1. A hydrogen sulfate salt of a compound of formula I

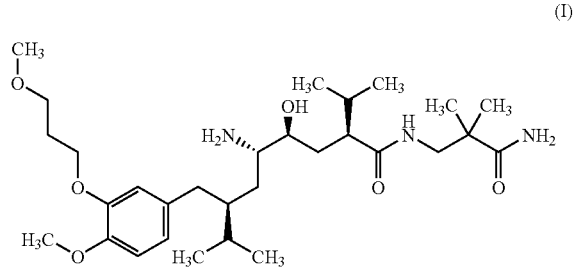

(I)

in crystalline form, said salt characterised by
(i) an X-ray powder pattern taken with a powder diffractometer comprising the following interlattice plane intervals:
d in [Å] (±0.1 Å): 21.3, 12.4, 10.7, 10.1, 8.4, 7.9, 6.7, 6.0, 5.3, 4.9, 4.7, 4.5, 4.4, 4.1; or
(ii) an ATR-IR spectrum having the following absorption bands expressed in reciprocal wave numbers ($cm^{-1}$): 3353 (br), 3078, 2960, 2935, 2876, 1660 (C=O), 1516

(amid II), 1470, 1444, 1425, 1389, 1371, 1260, 1234 (Aryl-O), 1191, 1163, 1140, 1047, 872, 809, 768, 723.

2. A pharmaceutical composition comprising a compound according to claim 1 and a pharmaceutically acceptable excipient or additive.

3. A pharmaceutical composition according to claim 2, containing a salt according to claim 1 in combination with at least one component selected from the group consisting of a:
 (i) HMG-Co-A reductase inhibitor or a pharmaceutically acceptable salt thereof,
 (ii) angiotensin converting enzyme (ACE) Inhibitor or a pharmaceutically acceptable salt thereof,
 (iii) calcium channel blocker or a pharmaceutically acceptable salt thereof,
 (iv) aldosterone synthase inhibitor or a pharmaceutically acceptable salt thereof,
 (v) aldosterone antagonist or a pharmaceutically acceptable salt thereof,
 (vi) dual angiotensin converting enzyme/neutral endopeptidase (ACE/NEP) inhibitor or a pharmaceutically acceptable salt thereof,
 (vii) endothelin antagonist or a pharmaceutically acceptable salt thereof,
 (viii) angiotensin II receptor blockers (ARB) or a pharmaceutically acceptable salt thereof, and
 (ix) diuretic or a pharmaceutically acceptable salt thereof.

4. Process for the manufacture of a salt according to claim 1, characterized in that
 (i) aliskiren free base is dissolved in an organic solvent,
 (ii) sulfuric acid is added to the solution obtained in (i),
 (iii) the solution left standing to induce crystallization,
 (iv) the crystals are filtered and dried, to obtain the salt.

5. The process of claim 4 wherein the sulphuric acid is an aqueous solution.

* * * * *